United States Patent [19]
Bach et al.

[11] Patent Number: 5,770,073
[45] Date of Patent: Jun. 23, 1998

[54] COMBINED CARDIOTOMY AND VENOUS RESERVOIR

[75] Inventors: Ulf-Eiel F. Bach, Minnetonka; James Strom, Arden Hills, both of Minn.

[73] Assignee: Minntech Corporation, Minneapolis, Minn.

[21] Appl. No.: 616,719

[22] Filed: Mar. 15, 1996

[51] Int. Cl.$^6$ ............................ A61M 1/14; B01D 27/00; B01D 29/00

[52] U.S. Cl. ...................... 210/472; 210/436; 210/437; 210/438; 210/485; 210/489; 422/44; 422/45; 422/47

[58] Field of Search ............................ 210/256, 436, 210/437, 438, 439, 458, 472, 485, 489, 499, 484, 498; 422/44, 45, 47; 604/4, 317, 319, 403

[56] References Cited

U.S. PATENT DOCUMENTS

| | | |
|---|---|---|
| 3,768,653 | 10/1973 | Brufield .................................. 210/188 |
| 3,770,129 | 11/1973 | Brumfield ............................... 210/232 |
| 3,907,504 | 9/1975 | Hammond et al. . | 
| 3,927,980 | 12/1975 | Leonard . |
| 4,026,669 | 5/1977 | Leonard et al. . |
| 4,033,345 | 7/1977 | Sorenson et al. . |
| 4,151,088 | 4/1979 | Wolf, Jr. et al. ........................ 210/180 |
| 4,158,693 | 6/1979 | Reed et al. ................................ 422/46 |
| 4,160,801 | 7/1979 | Badolato et al. ........................ 422/46 |
| 4,179,364 | 12/1979 | Bratten et al. ........................... 422/48 |
| 4,396,584 | 8/1983 | Burgess et al. .......................... 422/47 |
| 4,424,190 | 1/1984 | Mather, III et al. ..................... 422/46 |
| 4,428,743 | 1/1984 | Heck ......................................... 604/4 |
| 4,451,562 | 5/1984 | Elgas et al. ............................... 422/46 |
| 4,466,804 | 8/1984 | Hino ........................................... 604/4 |
| 4,490,331 | 12/1984 | Steg, Jr. ................................... 422/46 |
| 4,568,366 | 2/1986 | Frederick et al. ...................... 604/406 |
| 4,599,093 | 7/1986 | Steg, Jr. ................................... 422/46 |
| 4,615,694 | 10/1986 | Raines ..................................... 604/406 |
| 4,620,965 | 11/1986 | Fukusawa et al. ...................... 422/46 |
| 4,622,032 | 11/1986 | Katsura et al. ............................ 604/4 |
| 4,642,089 | 2/1987 | Zupkas et al. ............................. 604/4 |
| 4,664,682 | 5/1987 | Monzen .................................. 210/188 |
| 4,698,207 | 10/1987 | Bringham et al. ........................ 422/46 |
| 4,705,497 | 11/1987 | Shitaokoshi et al. ...................... 604/4 |
| 4,717,377 | 1/1988 | Fukasawa ................................... 604/4 |
| 4,734,269 | 3/1988 | Clarke et al. ............................. 422/47 |
| 4,737,139 | 4/1988 | Zupkas et al. .............................. 604/4 |
| 4,743,371 | 5/1988 | Servas et al. ........................... 210/188 |
| 4,756,705 | 7/1988 | Beijbom et al. ............................ 604/4 |
| 4,765,959 | 8/1988 | Fukasawa ................................. 422/48 |
| 4,818,490 | 4/1989 | Carson et al. ............................ 422/46 |
| 4,863,452 | 9/1989 | Irmitter et al. ......................... 604/408 |
| 4,954,251 | 9/1990 | Barnes et al. ........................... 210/806 |
| 4,954,317 | 9/1990 | Raible ...................................... 422/46 |
| 4,959,062 | 9/1990 | Gellman .................................. 604/403 |
| 4,964,984 | 10/1990 | Reeder et al. .......................... 210/436 |
| 4,976,708 | 12/1990 | Oshiyama ............................... 604/408 |
| 5,000,764 | 3/1991 | Oshiyama et al. ..................... 210/188 |
| 5,026,525 | 6/1991 | Katsura .................................... 422/45 |

(List continued on next page.)

*Primary Examiner*—John Kim
*Attorney, Agent, or Firm*—Cushman Darby & Cushman Intellectual Property Group of Pillsbury Madison & Sutro, LLP

[57] ABSTRACT

A combined venous and cardiotomy blood reservoir is provided that includes a rigid shell having a top, a bottom, and a continuous side wall. The top and bottom walls are connected to the continuous side walls so as to define a reservoir for venous and cardiotomy blood. A double column structure is provided within the blood reservoir, the first column for receiving and degassing venous blood, the second for receiving, filtering and defoaming cardiotomy blood. The venous blood filtering and defoaming components can include a top venous screen plate, a bottom venous screen plate or stand and a perforated venous cage captured therebetween. The venous column is of generally D-shape and has a double screen structure including an inner microscreen and an outer microscreen received respectively on the inside and outside of the perforated venous cage. The cardiotomy blood filtering and defoaming components can include an inner, first defoaming element, a core support frame, a depth filter, an outer, second defoaming element, and a filter covering sock.

11 Claims, 6 Drawing Sheets

U.S. PATENT DOCUMENTS

| | | | |
|---|---|---|---|
| 5,034,188 | 7/1991 | Nakanishi et al. | 422/46 |
| 5,039,430 | 8/1991 | Corey, Jr. | 210/806 |
| 5,039,486 | 8/1991 | Gordon | 422/46 |
| 5,049,146 | 9/1991 | Bringham et al. | 604/4 |
| 5,055,198 | 10/1991 | Shettigar | 210/650 |
| 5,061,236 | 10/1991 | Sutherland et al. | 604/4 |
| 5,087,250 | 2/1992 | Lichte et al. | 604/4 |
| 5,112,480 | 5/1992 | Hukasawa | 210/188 |
| 5,120,302 | 6/1992 | Vescovini et al. | 604/4 |
| 5,127,900 | 7/1992 | Schickling et al. | 604/4 |
| 5,149,318 | 9/1992 | Lindsay | 604/4 |
| 5,158,533 | 10/1992 | Strauss et al. | 604/4 |
| 5,160,332 | 11/1992 | Nomura | 604/4 |
| 5,167,921 | 12/1992 | Gordon | 422/45 |
| 5,192,439 | 3/1993 | Roth et al. | 210/485 |
| 5,196,166 | 3/1993 | Kasura | 422/45 |
| 5,221,474 | 6/1993 | Yokono et al. | 210/436 |
| 5,240,677 | 8/1993 | Jones et al. | 422/46 |
| 5,266,265 | 11/1993 | Raible | 422/46 |
| 5,282,783 | 2/1994 | Lindsay | 604/4 |
| 5,308,483 | 5/1994 | Sklar et al. | 210/232 |
| 5,318,510 | 6/1994 | Cathcart | 604/4 |
| 5,352,218 | 10/1994 | Buckley et al. | 604/407 |
| 5,403,273 | 4/1995 | Lindsay | 604/4 |
| 5,411,705 | 5/1995 | Thor et al. | 422/45 |
| 5,439,587 | 8/1995 | Stankowski et al. | 210/436 |
| 5,458,567 | 10/1995 | Cathcart | 604/6 |
| 5,580,522 | 12/1996 | Leonard et al. | 422/46 |
| 5,601,714 | 2/1997 | Haveland | 210/436 |
| 5,632,894 | 5/1997 | White et al. | 210/436 |
| 5,683,355 | 11/1997 | Fini et al. | 210/436 |

COMBINED CARDIOTOMY AND VENOUS RESERVOIR

BACKGROUND OF THE INVENTION

1. Field of the Invention

The present invention relates to a combined cardiotomy and venous reservoir and in particular to a rigid side walled, double column combined cardiotomy and venous reservoir constructed and arranged to provide an increased surface area for blood filtering, and improved structure for capturing and channeling air.

2. Description of the Related Art

A venous reservoir and a cardiotomy reservoir are typically included in a cardiopulmonary bypass circuit.

The venous reservoir accommodates for variations in blood volume when cardiopulmonary bypass flow is connected through a membrane oxygenator, and separates the bubbles from the venous blood and vents such separated gas to atmosphere.

The cardiotomy reservoir reclaims blood drawn from the surgical site by defoaming and filtering the blood to remove foreign matter. More particularly, during a cardiopulmonary bypass operation, it is essential to suction away the various fluids, including for example, air, debris such as bone chips, blood, saline solution, liquids applied to the heart and the like. This must be accomplished as quickly and efficiently as possible without causing injury to the patient. Such fluids are termed cardiotomy blood and require filtration prior to reinfusion. Normally, a cardiotomy reservoir is used in conjunction with relatively high vacuum suction in order to remove and collect cardiotomy blood and other liquids as quickly as possible. Blood collected within a cardiotomy reservoir can be filtered and defoamed to remove air, debris and clots after which it can be reinfused to the patient.

Typically, before it is oxygenated and returned to the body, blood which has been defoamed and filtered in a cardiotomy reservoir is combined with blood extracted from the patient's venous system.

To simplify the components and connections and to reduce the volume of such extracorporeal blood circuits, it has been proposed that cardiotomy blood and venous blood be combined in a single reservoir which replaces the separate cardiotomy reservoir and separate venous reservoir formerly used and that the combined fractions be directly fed to an oxygenator.

This creates some problems since the flow rate of venous blood into the extracorporeal circuit is several times, on the order of three times, greater than the flow of cardiotomy blood. Moreover, the venous blood is substantially clean requiring only minimal defoaming and filtration. When venous blood is subjected to the same filtration as that used for cardiotomy blood, it is detrimental to the blood cells. Indeed, the depth filter media used in modern cardiotomy reservoirs can damage healthy cells, especially under high pressures and, therefore, blood obtained directly from a venous shunt which is uncontaminated by foreign matter should not be forced through such filter media, if possible. Thus, it would be desirable to avoid forcing blood derived from the patient's venous system through a conventional cardiotomy reservoir.

In order to overcome this problem, in recent years separate filter chambers have been provided within a single apparatus to provide for separate filtering for venous blood and cardiotomy blood. Such a device is described in U.S. Pat. No. 4,642,089. This device comprises a hollow chamber of rigid material. The filter chamber contains two separate chambers, an upper chamber for introduction and filtration of cardiotomy blood through a non-woven depth filter and a defoaming material and a lower chamber including a defoaming material but free of the non-woven depth filter. Cardiotomy blood enters the upper filter chamber from the top of the unit and venous blood enters the lower filter chamber through the bottom of the unit. Blood entering either chamber passes through the filter and/or defoamer and is combined in a space defined by the outer walls and the filter chamber where it can be withdrawn for reinfusion to the patient.

There are several drawbacks associated with the cardiotomy/venous unit of the '089 patent. For example, venous blood which is normally obtained by gravity flow enters the unit from the bottom where it passes through the defoaming filter prior to discharge through a bottom discharge port. A disadvantage of this is that there is resistance to entry of venous blood.

Combined cardiotomy and venous return reservoirs which provide separate flow paths into common collection reservoirs for venous return blood and for cardiotomy blood are also described in U.S. Pat. Nos. 4,705,497 and 4,737,139. U.S. Pat. No. 4,705,497 describes a combined cardiotomy and venous return reservoir in which the venous blood does not pass through any filtering or defoaming element and in which the venous and cardiotomy blood separately enter a pooling reservoir at different levels.

U.S. Pat. No. 4,737,139 provides a device in which cardiotomy blood is filtered through a reticulated polyurethane foam defoaming element, a felt depth filter and a mesh fabric screen, whereas the venous blood is only passed through the polyurethane foam and mesh fabric elements. The device is constructed and arranged such that the venous and cardiotomy blood fractions have separate flow paths into a common reservoir with venous blood entering the common collection reservoir below the cardiotomy blood. This flow pattern may result in significant layering of the blood especially since the exit port is at the bottom of the collection reservoir and the venous blood typically is fed into the device at a much higher rate than the cardiotomy blood.

Another combined cardiotomy and venous return reservoir structure is described in U.S. Pat. No. 5,039,430. In that system, blood is passed from the surgical site through a first defoaming element and a depth filter element to produce a filtered blood fraction. The filtered blood fraction is then combined with venous source blood to produce a combined blood fraction. The combined blood fraction is then mixed by passing it through a second defoaming element. The device of the '430 patent provides for such filtering and combining by nesting a combined chamber for cardiotomy and venous blood within an intermediate blood fraction mixing chamber which is in turn nested within an outer collection and return reservoir. Another integrated venous/cardiotomy reservoir is disclosed in Patent No. 5,411,705.

Some of these prior art reservoirs have blood flow paths that either cause blood stagnation or trap gas bubbles in the blood.

SUMMARY OF THE INVENTION

The present invention provides a combined venous and cardiotomy reservoir that provides for a simpler, less expensive and more efficient blood filtration, defoaming and storage for both venous and cardiotomy blood. The present invention advantageously minimizes areas where blood may stagnate and significantly enhances the escape of gas from the blood. Moreover, the present invention provides blood defoaming filters treated with anti-foam agent disposed so as to generally minimize the contact of blood with the filters.

According to the invention a combined venous and cardiotomy blood reservoir is provided that comprises a rigid shell having a top, a bottom, and a continuous side wall. The top and bottom walls are connected to the continuous side walls so as to define a reservoir for venous and cardiotomy blood. A double column structure is provided within the blood reservoir, the first column for receiving and degassing venous blood, the second for receiving, filtering and defoaming cardiotomy blood.

In an embodiment of the invention, the venous blood filtering and defoaming components include a top venous screen plate, a bottom venous screen plate or stand and a perforated venous cage captured therebetween. The venous column is of generally D-shape and has a double screen structure including an inner microscreen and an outer microscreen received respectively on the inside and outside of the perforated venous cage.

In an embodiment of the invention, the cardiotomy blood filtering and defoaming components include an inner, first defoaming element, a core support frame, a depth filter, an outer, second defoaming element and a filter covering sock.

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures.

DETAILED DESCRIPTION OF THE PRESENTLY PREFERRED EXEMPLARY EMBODIMENTS

Figure 1:
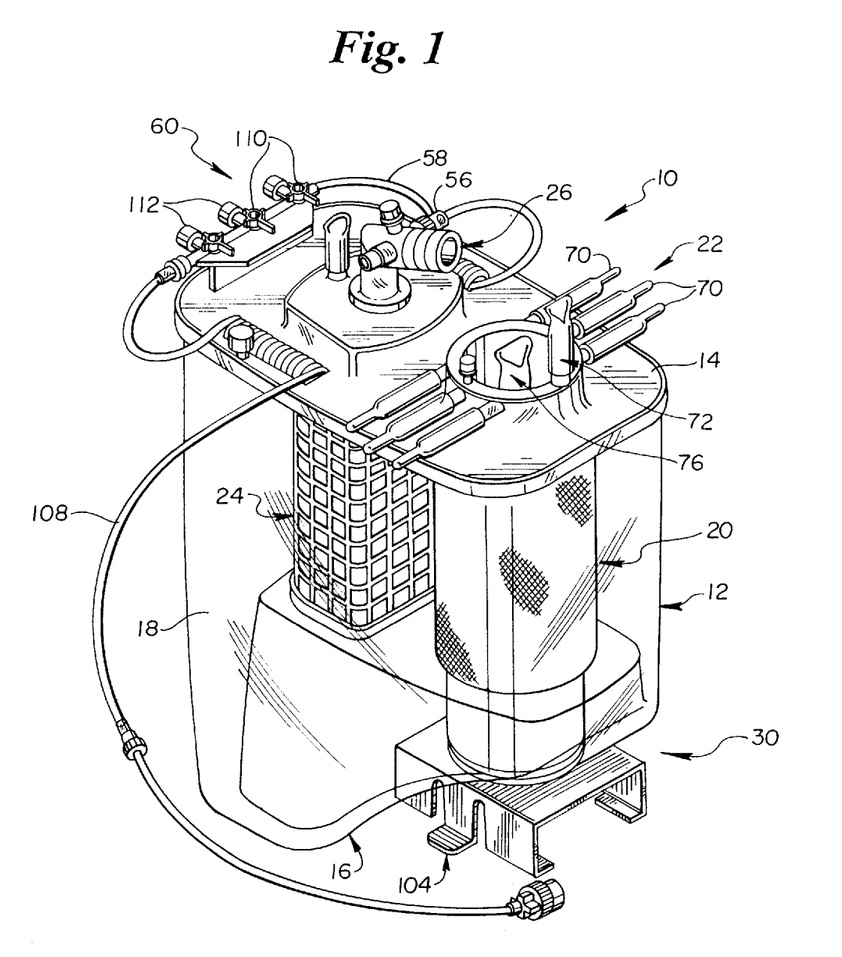
FIG. 1 is a perspective view of a combined venous/cardiotomy reservoir 10 in accordance with the present invention.

Referring to FIG. 1, a combined venous and cardiotomy blood reservoir 10 in accordance with the present invention is shown. The reservoir 10 includes a rigid shell 12 having a top 14, a bottom 16 and a continuous side wall 18 which define an enclosed reservoir for blood to be oxygenated and returned to the patient. A column 20 for cardiotomy blood filtering and defoaming is disposed within the reservoir 10 and is in fluid communication with a cardiotomy blood inlet shown generally at 22. A column 24 for venous blood filtering and defoaming is also located in the reservoir space. The venous blood filtering and defoaming unit or column 24 is spaced from the cardiotomy blood filtering and defoaming column 20 and is in fluid communication with a venous blood inlet 26.

A blood outlet 28 is in fluid communication with blood stored in the reservoir for discharging combined venous and cardiotomy blood.

A mounting bracket or holder 30 is connected to the bottom 16 of the reservoir assembly for connecting the reservoir 10 to a support stand or other component of the extracorporeal circuit. In the presently preferred embodiment the mounting bracket or holder 30 is used to connect the reservoir to an oxygenator 32 (FIG. 8) to provide a reservoir/oxygenator unit.

Figure 7:
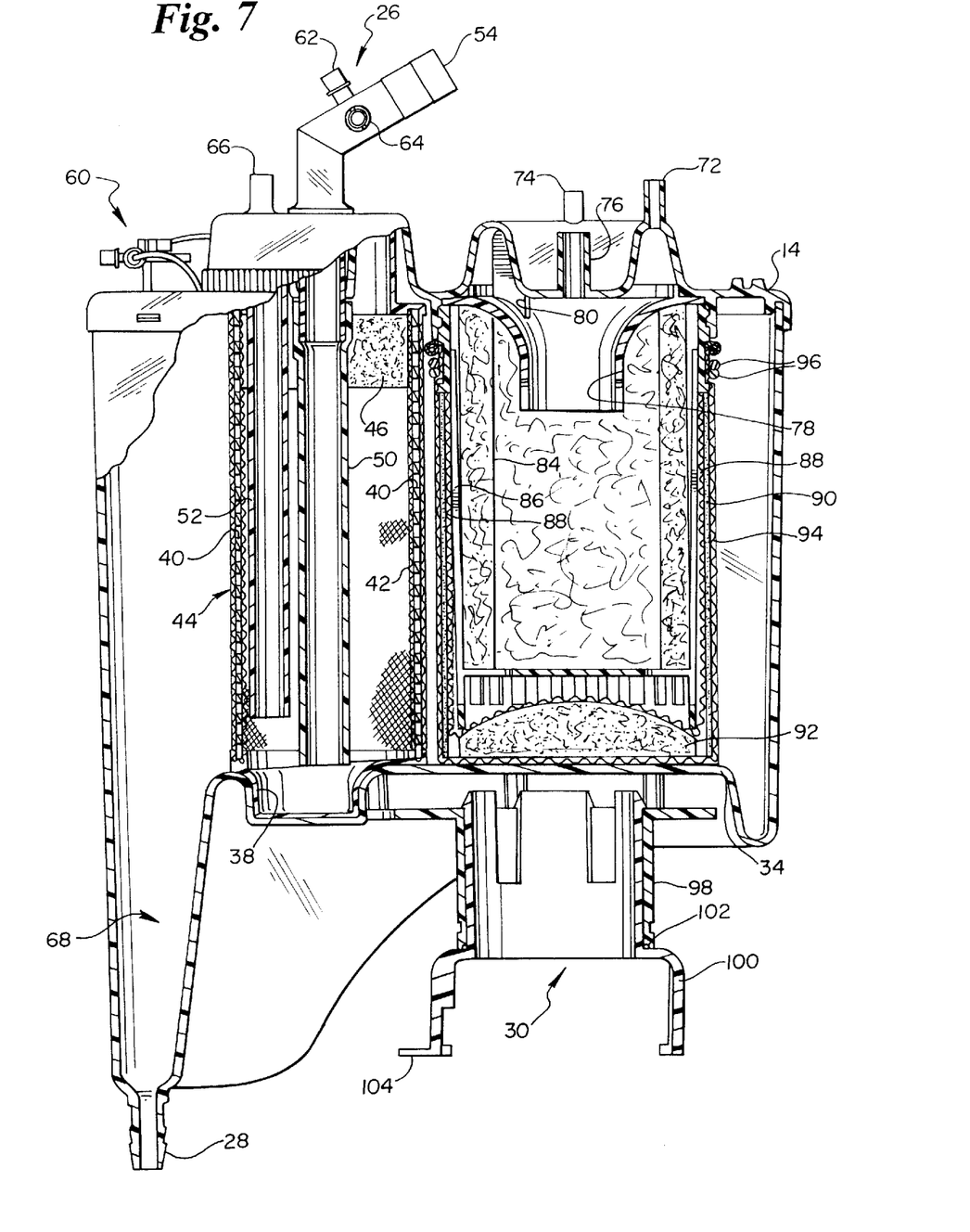
FIG. 7 is a partially cut away view of the cardiotomy/venous reservoir of the invention.

With reference to FIGS. 1 and 7 it can be seen that the combined cardiotomy/venous reservoir 10 comprises a rigid housing. The rigid shell is made of molded plastic, e.g. polycarbonate, or other suitable material that does not expand or contract when the shell receives or discharges blood. Moreover, in the illustrated and currently preferred embodiment the side wall 18 and bottom 16 are integrally formed, molded plastic whereas the top 14 is a separate plastic lid that is secured to the top edge of the side wall 18 in a suitable manner.

As can be seen, the top 14 is generally planer and the bottom wall 16 is recessed to define a planer pedestal 34 for supporting the venous blood filtering and defoaming column 24 and on which the cardiotomy column 20 is seated. The pedestal 34 is generally parallel to the top. In the event the volume of blood within the reservoir drops below a prescribed level, the upper surface of the pedestal structure will become exposed and thus indicates the blood level and the volume of blood remaining in the reservoir. The shell is preferably substantially clear so that medical personnel can observe the blood level within the reservoir. As noted below, in accordance with the invention, the bottom venous screen stand 38 is configured and cooperates with the inlet tube 50 to define an anti-syphon structure so that even if the blood level drops below a prescribed level, the system will not need to be re-primed.

A substantial portion of the bottom 16 of the container slopes away from the top and from the pedestal towards blood outlet 28 which is most remote or farthest from the top 14. The gently inclined bottom 16 of the reservoir encourages the flow of blood to be directed outwardly. Thus, blood flowing either through the cardiotomy blood inlet 22 or the venous blood inlet 26 will flow through the respective filter structures and then downward towards the blood outlet, minimizing areas where blood might stagnate. Filtered and degassed blood flows e.g. by gravity, through the bottom disposed outlet 28 (FIG. 2) for removal of blood for oxygenation and reinfusion.

As noted above, the venous blood filtering and defoaming column 24 is independent of and disposed in parallel side-by-side relation to the cardiotomy column 20. The venous column 24 extends from the top 14 to the bottom 16 of the hard reservoir defining shell. Because the venous blood generally does not contain the bone fragments and other surgical waste found in cardiotomy blood, but may include gas bubbles or other emboli that must be filtered, filtering and defoaming is provided but no depth filter is provided.

Figure 2:
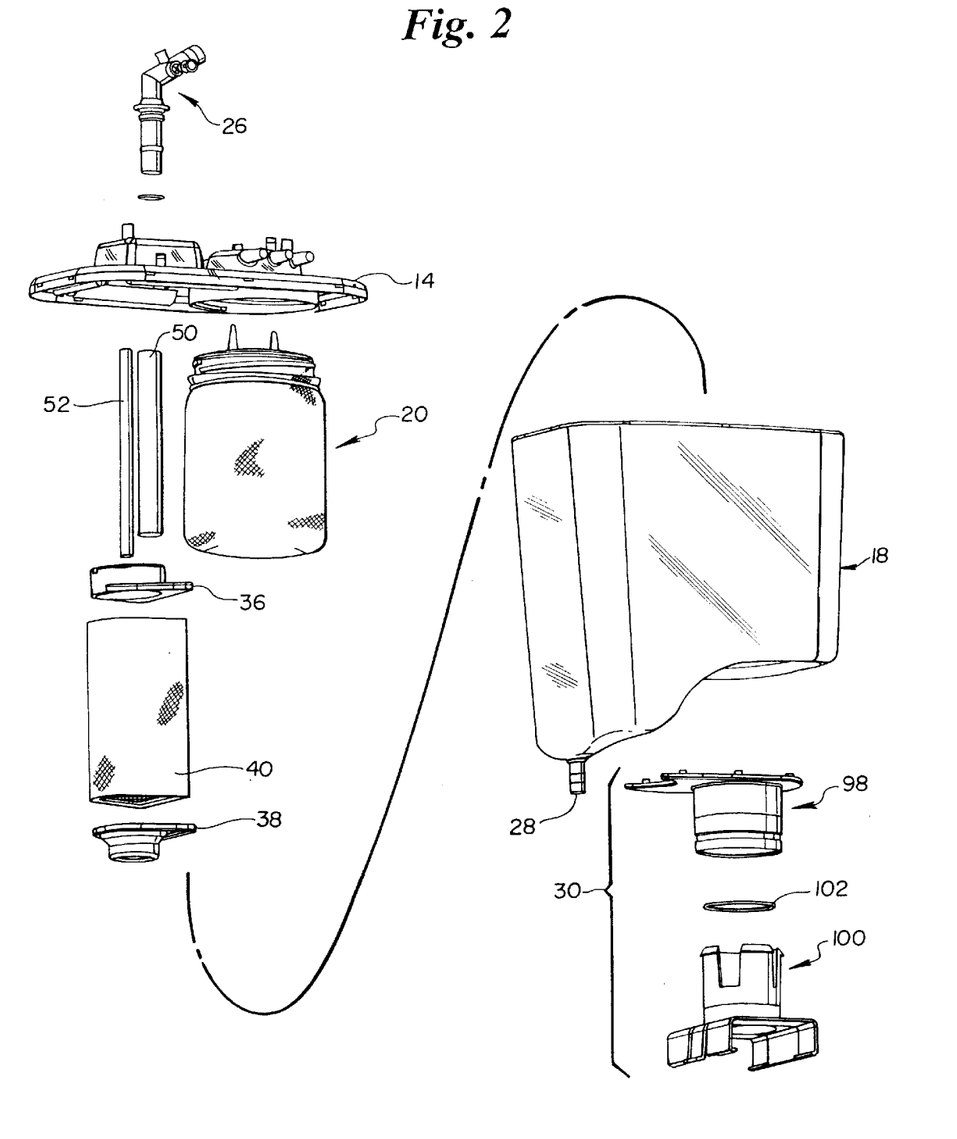
FIG. 2 is an exploded view of the combined venous/cardiotomy reservoir of the invention.
Figure 3:
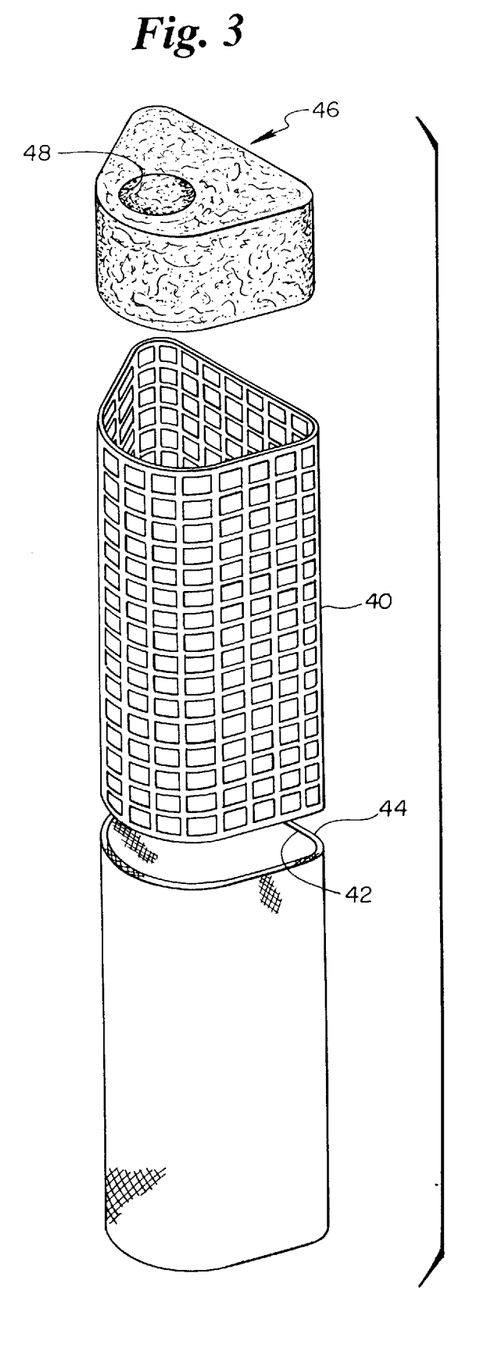
FIG. 3 is an exploded perspective view of the venous blood receiving and defoaming column.
Figure 4:
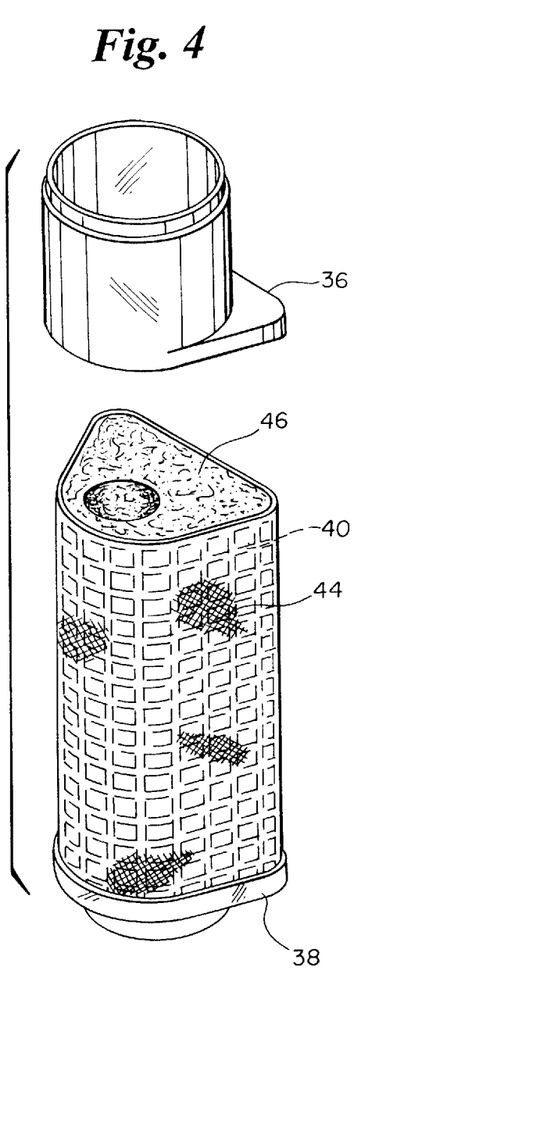
FIG. 4 is a perspective view of the assembled venous column.

As can be seen in FIG. 2, the venous column includes a top venous screen plate 36, a bottom venous screen plate or stand 38 and a perforated venous cage 40 captured therebetween. The venous cage 40 is illustrated more particularly in the exploded view of FIG. 3. The stand 38 is configured and cooperates with inlet tube 50 so that tube 50 has a bottom opening vertically below the top edge of stand 38 and stand 38 defines a chamber or pocket for fluid. Thus, even if the fluid level in the reservoir drops below the top edge of stand 38, the bottom opening of tube 50 will be disposed in the residual fluid in the pocket or chamber of stand 38 and tube 50 will remain fluid filled.

The venous column is of generally D-shape in horizontal cross-section and has a double screen structure including an inner microscreen 42 and an outer microscreen 44 received respectively on the inside and outside of the perforated venous cage 40. In a preferred embodiment, each of the inner and outer venous microscreens is, for example, a polyester screen having a pore size in the range of 50–150 micrometers and preferably about 105 micrometers. Such a double screen structure provides a greater surface area for blood filtration, is a less expensive configuration than other generally available systems and advantageously creates a column defined by the perforated venous cage, between the inner and outer microscreens which facilitates the capture and removal of air from the blood. Indeed as blood flows through the inner and outer microscreens via the perforated venous cage 40, air is captured therebetween and channeled upwardly.

The inner microscreen 42 (FIGS. 3 and 7) receives in the upper portion thereof a defoaming element 46 complimentarily shaped to the cross sectional configuration of the perforated venous cage 40. The defoamer includes a preformed aperture 48 for receiving the venous blood inlet tube 50 and a recirculation tube 52, as described more particularly below.

The eccentric, D-shaped configuration of the venous column 24 advantageously insures, via the aperture 48 defined in the defoamer for the venous inlet tube 50, proper disposition of the venous inlet tube 50 relative to the remainder of the venous column 24 and within the reservoir 10 as a whole.

In the preferred embodiment, the venous defoaming element 46, like the cardiotomy defoaming elements described below, is preferably made of thermally reticulated polyurethane foam having a pore size in the range of 5 to 50 ppi, and treated with an anti-foam agent (e.g. Dow silicone antifoam). Defoaming element 46 extends from top plate 36 partially, e.g. about 1 to 2 inches, toward bottom plate 38. The bottom edge of defoaming element 46 is above the standard operating fluid level of reservoir 10 to minimize the exposure of the blood to the defoaming agent(s).

Venous blood flows from venous inlet 26 into inlet tube 50. Inlet tube 50 is medical grade plastic tubing having, for example, a one-half inch inner diameter. Inlet tube 50 extends from venous inlet 26 at top plate 36 to proximate bottom plate 38, at pedestal 34.

Blood inlet 26 has a port 54 for connection to a supply line of venous blood from the patient, a smaller return port 56 for connection to return line 56 of a sampling access device 60, described in greater detail below. Moreover, a venous sample port 62 is provided, as is a port 64 for a temperature probe.

A rapid prime port 66 which is fluidly coupled to the recirculation tube 52 is advantageously provided adjacent the venous inlet port 26. More particularly, in advance of use, the entire extracorporeal system is primed with a crystalloid solution, e.g. saline. The rapid prime port is used to facilitate priming the reservoir. Thus a source of priming solution is coupled to the rapid prime port and flows into the reservoir through the recirculation tube 52. In addition or in the alternative, a priming solution may be directed into the cardiotomy column through port 72 thereof.

One or more additional ports may be provided for coupling other sources of venous blood or for selectively coupling other monitoring equipment or sample access devices.

The venous blood received in the venous column passes through inner microscreen 42, through the perforated venous cage 40 and through the outer microscreen 44. Meanwhile, gas passes upwardly in the venous column so that filtered and degassed blood enters the storage compartment of the reservoir 10 and is permitted to pass by gravity to the collection segment 68 and outwardly of the reservoir for oxygenation and ultimate reinfusion to the patient.

The cardiotomy blood filtering and defoaming column 20 provided in accordance with the invention extends generally substantially from the top 14 to the bottom pedestal 34 of the reservoir structure. The cardiotomy column 20 serves to trap bone fragments, cartilage, and surgical waste from the cardiotomy blood collected at the surgical site, as well as emboli trapped in the blood.

The cardiotomy column 20 includes a plurality of cardiotomy inlets or ports 70 which may be selectively coupled to aspiration tubing as needed. Pumps (not shown) are utilized in conjunction with the tubing connected to cardiotomy ports 70 to direct cardiotomy blood from the surgical site to the cardiotomy column 20. A fitted ¼ inch inlet 72, a luer port 74, as well as a ⅜ inch filtered inlet 76, for an auxiliary cardiotomy reservoir or post operative chest drainage, are all provided for directing fluids into the cardiotomy column. As shown, covers are provided over unused ports to maintain sterility.

Figures 5, 6:
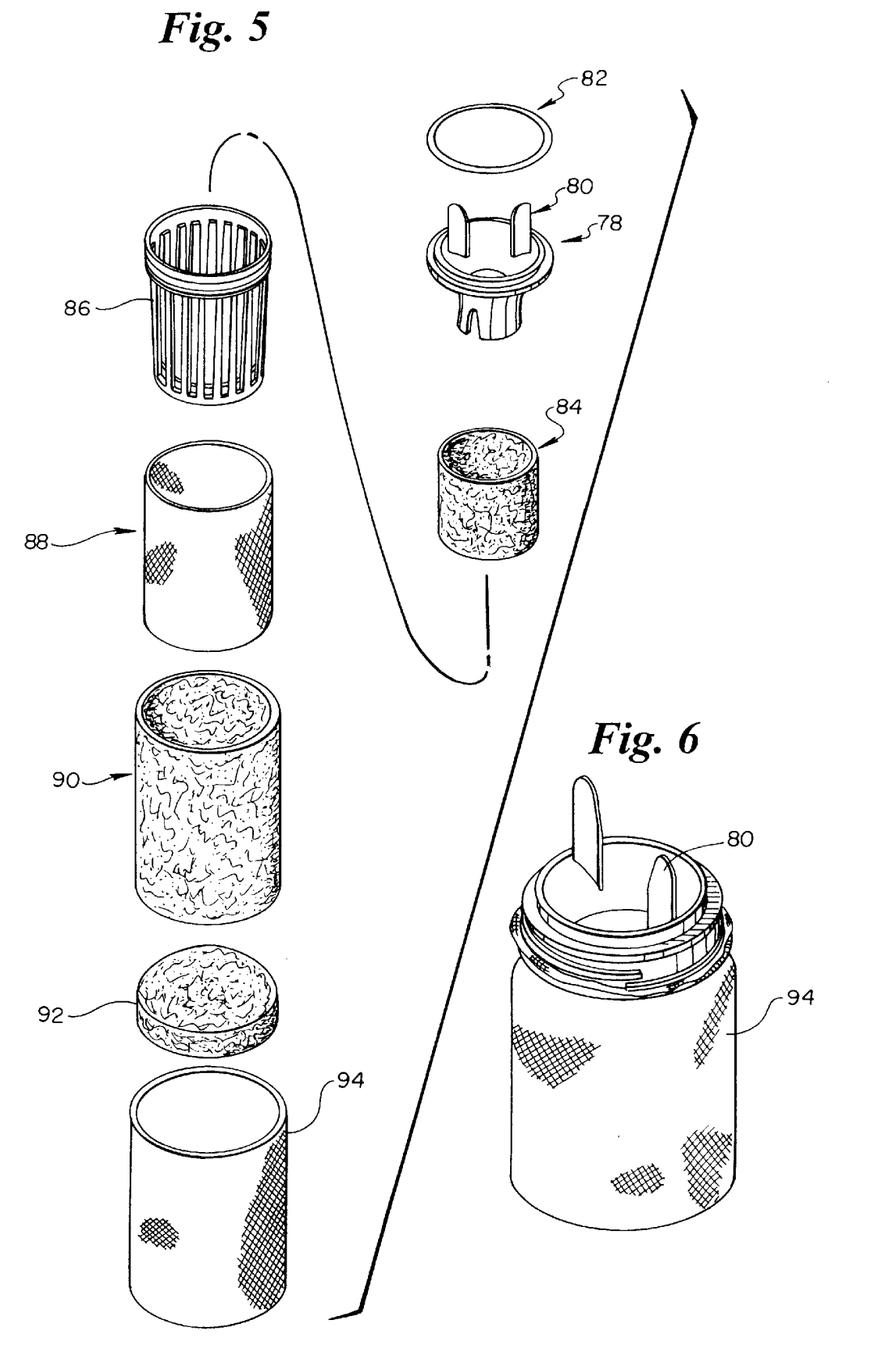
FIG. 5 is an exploded perspective view of the components comprising the cardiotomy column in accordance with the invention.
FIG. 6 is an assembled perspective view of the cardiotomy column.

The exploded cardiotomy structure may be seen in FIG. 5. A deflector structure 78 including upright baffles 80 is provided at the upper end of the cardiotomy column 20 to direct blood flow into the center of the cardiotomy column. An 0-ring 82 is provided to seal the deflector 78 with respect to the rigid housing. Thus, the blood, debris, and the like is received into the interior of the cardiotomy column. Blood is passed through an inner, first defoaming element 84, a core support frame 86, a depth filter 88, an outer, second defoaming element 90 and ultimately through a filter covering sock 94.

In an exemplary embodiment, the first defoaming element 84 is an open cell, blood compatible, synthetic polymeric foam material to collapse blood foam into fluid blood. For example, the first defoaming element 84 may be formed of a thermally reticulated polyurethane foam having a pore per inch (ppi) size in the range of 5–50 ppi. The first defoaming element may be treated with an anti-foam agent to facilitate defoaming. Suitable anti-foam agents are known in the industry and include silicone anti-foams.

The first defoaming element 84 is received within and supported by the perforate, plastic core frame 86. Surrounding the core 86 and extending substantially from the top to the bottom of the reservoir chamber is a cardiotomy filter element 88. In the illustrated embodiment the filter element 88 has a closed bottom and open top. Thus, the cardiotomy filter 88 fully receives the core 86 and the inner defoamer 84 disposed therewithin (see FIG. 7). Filter element 88 is for example, a 20 micron depth filter made from dacron polyester felt having a mean aperture size in the range of 20–50 microns.

Surrounding the cardiotomy filter 88 is a second defoaming element 90 which may be of substantially the same composition as the inner defoamer 84. The second defoaming element 90 may be of the same, greater or lesser thickness than the first defoaming element. To exemplify this fact, in FIG. 5 elements 84 and 90 have generally the same thickness, or element 90 could be seen to have a slightly greater thickness whereas in the illustration of FIG. 7, the first defoamer 84 is shown as having a notably greater thickness than element 90. There may be some advantage to providing a relatively thick first defoamer because, e.g., it may be found to better maintain its shape and desired disposition in use.

A bottom foam component 92 is also provided, outside depth filter 88 but surrounded by defoamer 90 and captured by sock 94. Bottom foam component 92 is provided to ensure that blood entering and passing through the cardiotomy column passes through st least one defoamer. As an alternative to providing a separate foam component 92 as illustrated, the second, outer defoaming element may be, e.g., cup shaped, so as to have an integral foam bottom.

Finally, as a final filter to filter both matter and debris, a knitted polyester filter cover sock 94 captures the entirety of the cardiotomy assembly. The filter cover 94 is preferably coated with surfactant and is secured with respect to the core by O-ring(s) 96.

Once the blood has passed through the inner defoamer 84, core 86, depth filter 88, outside defoamer 90 and filter cover or sock 94, the blood has been sufficiently filtered and degassed to permit its mixing with the venous blood which occurs within the blood storage compartment of the reservoir 10.

Figure 8:
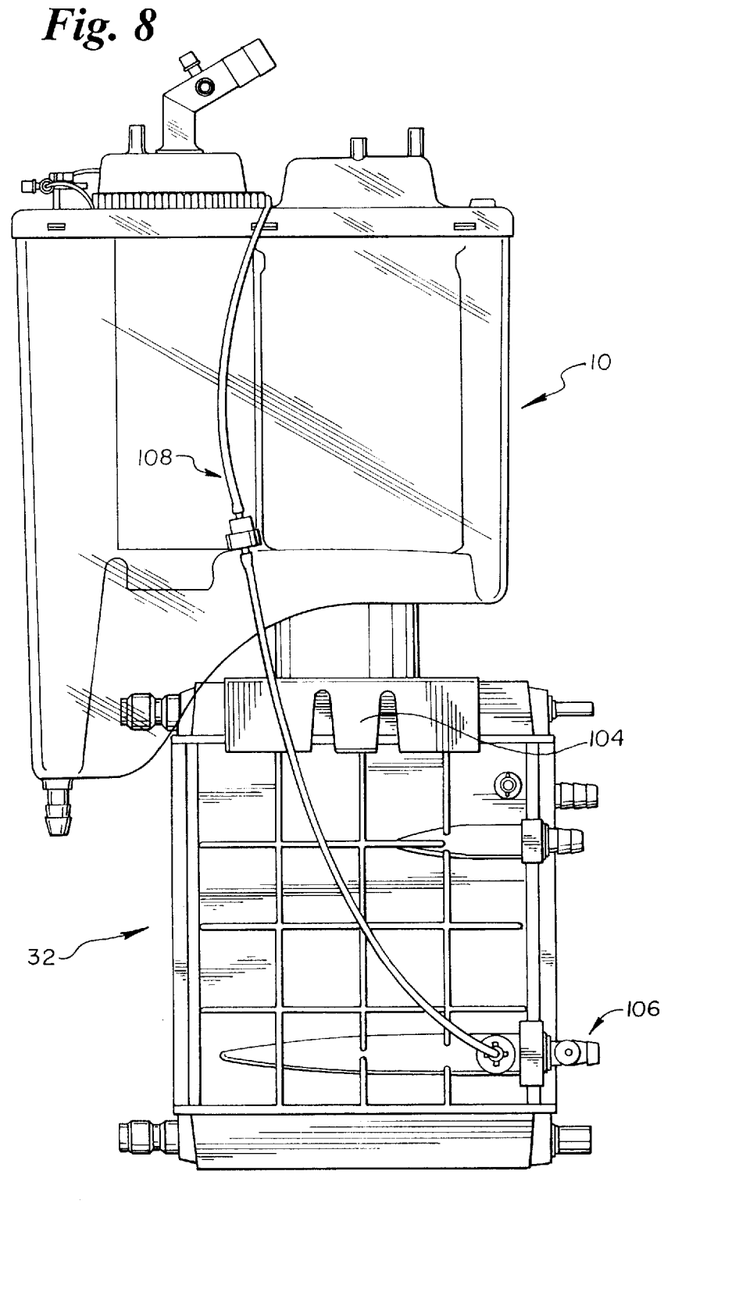
FIG. 8 is a side elevational view thereof illustrating the assembly of the cardiotomy/venous reservoir to an oxygenator.

Referring to FIG. 8, the reservoir 10 of the invention is preferably molded as a discrete unit. However, the blood reservoir is preferably, advantageously attached to an oxygenator via a holder 30.

More particularly, a coupling 98 is secured to or formed with the bottom wall 16 (pedestal 34) of the reservoir structure. See FIG. 2. In the illustrated embodiment, an adapter 100 is inserted into and lockingly engaged with the coupling 98, with an O-ring 102 therebetween. This enables an adapter to be selected that corresponds to a separately formed oxygenator, whereby the reservoir can be coupled to any one of a variety of oxygenators.

Thus, the adaptor 100 is formed to cooperatively engage and preferably lock at the bottom end thereof to an upper surface of an oxygenator. In the illustrated embodiment, the oxygenator 32 is proprietary to the assignee of this invention and is of rectangular horizontal cross-section. In the illustrated embodiment, then, the adapter 100 is configured to engage a generally rectangular oxygenator. The adapter 100 is selectively locked to the oxygenator 32 by providing a release tab 104 which is selectively received between suitably disposed projections (not shown in detail) on the oxygenator. The adapter is slid horizontally along the top of the oxygenator. To release the adapter 100 from the oxygenator, the release tab 104 is pulled outwardly thereby disengaging the tab from the receiving projections and permitting the adapter to be slid horizontally with respect to the oxygenator and removed therefrom.

The oxygenator with which the reservoir is advantageously provided has a horizontally oriented oxygenated blood outlet 106. A recirculation line 108,58 extends from the blood outlet 106 to the return port 56 for recirculating blood.

Referring to FIG. 1, sampling access device 60 is shown connected to sample supply line 108 and return line 58. Valve knobs 110 are shown with their associated sample ports 112. The three valves are connected in series between lines 108 and 58. In the configuration illustrated, the valve knobs are in the non-sampling position, permitting flow of oxygenated blood from tube 108 to tube 58.

In operation, oxygenated blood continuously flows through small diameter supply tube 108, sampler 60 and return line 58, e.g., at approximately 50 to 100 cc/min and samples can be selectively removed from access ports 110 on sampling device 60. Samples of oxygenated blood are supplied under pressure when any of the valve knobs are rotated e.g. 90 degrees.

In operation, reservoir 10 is connected to an extracorporeal blood circuit (not shown). Suction lines with pumps convey blood to cardiotomy blood inlet 70 which direct the cardiotomy blood into cardiotomy blood filtering and defoaming column 20.

Venous blood is drawn from the patient and passes into venous inlet 54. The venous blood flows from inlet 54 into inlet tube 50 which carries the blood toward bottom 38 so that the venous blood does not splash, which can damage the blood or allow gas bubbles to form in the blood. Venous blood then flows through the double filter assembly.

As noted above, the venous blood filtering and defoaming column includes venous defoaming element 46 similar to the first defoaming element in cardiotomy blood filtering and defoaming column 20. However, the venous defoaming element 46 is positioned adjacent to the top of venous blood filtering and defoaming column 24, above the normal operating level of the reservoir 10. Therefore, in normal operating conditions, fluid venous blood does not contact venous defoaming element 46, but venous blood foam sitting on top of the fluid venous blood contacts venous defoaming element 46, converting the blood foam to fluid blood. The filtered and defoamed cardiotomy blood and the filtered and defoamed venous blood simultaneously flow to and mix in collection segment or chamber 68 and ultimately flow out outlet 28 to the oxygenator 32 for oxygenation and ultimate return to the patient.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

What is claimed is:

1. A combined cardiotomy reservoir and venous reservoir, comprising:

a housing having a top, a bottom and continuous side walls formed of a material resisting expansion and collapse in use;

a venous column defined within said housing and including first filtration means for filtering body fluids;

a cardiotomy column defined within said housing and including second filtration means for filtering and defoaming body fluids, said cardiotomy column being independent of and laterally spaced from said venous column; and a plurality of ports communicating an interior of said housing and an exterior of said housing for the introduction and withdrawal of fluids, including at least one inlet port for blood and body fluids in communication with an interior of the cardiotomy column, at least one inlet port for blood and body fluids in communication with an interior of said venous column and at least one outlet port for blood in communication with a reservoir chamber of said housing that receives filtered fluid from said venous column and filtered and defoamed fluid from said cardiotomy column;

wherein said first filtration means comprises a perforated frame having a first microscreen provided adjacent an interior surface thereof and a second microscreen mounted to an exterior surface thereof.

2. The combination of claim 1, wherein said second filtration means comprises at least one defoaming element; a perforated core defining an interior fluid receiving compartment; a depth filter element and a filter sock disposed in surrounding relation to said at least one defoaming element, said core and said depth filter element.

3. The combination of claim 1, wherein said perforated frame is substantially D-shaped in horizontal cross-section.

4. The combination of claim 1, wherein said venous column further comprises a defoaming element mounted within said perforated frame and above a customary level of fluid within said venous column.

5. A combination of claim 1, further comprising a mounting bracket structure operatively coupled to a bottom of said housing for connecting the housing to a component of an extracorporeal circuit.

6. The combination of claim 5, wherein said bracket is constructed and arranged to couple the housing to an oxygenator structure.

7. A combined cardiotomy reservoir and venous reservoir, comprising:

a housing a top, a bottom and continuous side walls formed of a material resisting expansion and collapse in use;

a venous column defined within said housing and including first filtration means for filtering body fluids;

a cardiotomy column defined within said housing and including second filtration means for filtering and defoaming body fluids; and a plurality of ports communicating an interior of said housing and an exterior of said housing for the introduction and withdrawal of fluids, including at least one inlet port for blood and body fluids in communication with an interior of the cardiotomy column, at least one inlet port for blood in communication with an interior of said venous column and at least on outlet port for blood in communication with a reservoir chamber of said housing that receives filtered fluid from said venous column and filtered and defoamed fluid from asid cardiotomy column;

wherein said first filtration means comprises a perforated frame having a first microscreen provided adjacent an interior surface thereof, wherein said perforated frame is supported from below by an imperforate stand structure defines a residual fluid chamber and an inlet tube extends from said inlet port of said venous column at least partially into said residual fluid chamber, thereby to define an anti-syphon structure.

8. A device for defoaming and filtering venous blood for separating foam, macroscopic and microscopic air bubbles from venous blood, comprising:

a housing defining a reservoir for containing blood;

blood inflow and outflow ports in communication with said reservoir;

a first filter structure mounted within said housing and including a perforated cage, a first microscreen disposed within an interior of said cage, a second microscreen structure disposed exteriorly of said cage and a defoaming component of limited vertical height mounted to an upper portion of said cage structure, an inlet tube extending through said defoaming component from said inflow port to a bottom portion of said cage, whereby the upper portion of the first filter structure receives the foam, and macroscopic and microscopic bubbles separated from blood as it flows through the cage and microscreen structures and whereby contact of blood with said defoaming component is substantially avoided.

9. A device as in claim 8, wherein said perforated cage is substantially D-shaped in horizontal cross-section.

10. A device as in claim 8, wherein said perforated cage is supported from below by an imperforate stand structure that defines a residual fluid chamber, and said inlet tube extends from said inlet port at least partially into said residual fluid chamber, thereby to define an anti-syphon structure.

11. A combined venous/cardiotomy blood reservoir, comprising:

(a) rigid shell having a top, a bottom, and a continuous sidewall, said top and bottom being connected to the sidewall to form an enclosed reservoir;

(b) a cardiotomy filter assembly comprising a cardiotomy blood filter and a defoamer located within the reservoir, said cardiotomy blood filter and defoamer each extending substantially from the top to the bottom of the shell, and a cardiotomy blood inlet in fluid communication with the cardiotomy blood filter and defoamer;

(c) a venous filter assembly comprising a venous blood filter and a defoamer located within the reservoir laterally spaced from so as to be separate from and independent of the cardiotomy filter assembly, said venous blood filter extending substantially from the top to the bottom of the shell, and a venous blood inlet in fluid communication with the venous blood filter and defoamer;

(d) a blood outlet in fluid communication with the reservoir, wherein said cardiotomy defoamer comprises at least one defoaming element, and further comprising a perforated core defining an interior fluid receiving compartment in communication with said cardiotomy blood inlet and a depth filter element, and further comprising a sock filter disposed in surrounding relation to said at least one defoaming element, said core and said depth filter element.

\* \* \* \* \*

UNITED STATES PATENT AND TRADEMARK OFFICE
CERTIFICATE OF CORRECTION

PATENT NO. : 5,770,073
DATED : June 23, 1998
INVENTOR(S) : Bach, et al.

It is certified that error appears in the above-identified patent and that said Letters Patent is hereby corrected as shown below:

Column 9, line 30, delete "a housing a top,..." and substitute --a housing having a top,... -- therefor.

Column 9, line 45, delete "on" and substitute --one-- therefor.

Column 9, line 52, delete "thereof, wherein" and substitute --thereof, and a second microscreen mounted to an exterior surface thereof, wherein-- therefor.

Column 9, lines 53,54, delete "structure defines" and substitute --structure that defines-- therefor.

Signed and Sealed this

Thirteenth Day of October 1998

Attest:

BRUCE LEHMAN

Attesting Officer

Commissioner of Patents and Trademarks